United States Patent [19]

King

[11] Patent Number: 4,562,180

[45] Date of Patent: Dec. 31, 1985

[54] PESTICIDAL O-(N-ALKOXY-SUBSTITUTED-ORTHO-FLUORO-BENZIMIDOYL)-THIOPHOSPHONATES

[75] Inventor: William F. King, Novato, Calif.

[73] Assignee: Chevron Research Company, San Francisco, Calif.

[21] Appl. No.: 595,098

[22] Filed: Mar. 30, 1984

[51] Int. Cl.$^4$ .......................... A01N 57/14; C07F 9/40
[52] U.S. Cl. ...................... 514/114; 260/944
[58] Field of Search .................. 260/944; 424/211; 514/114

[56] References Cited

U.S. PATENT DOCUMENTS

| | | | |
|---|---|---|---|
| 3,760,041 | 9/1973 | Lorenz et al. | 260/944 |
| 3,872,185 | 3/1975 | Lorenz et al. | 260/944 |
| 4,054,650 | 10/1977 | Lorenz et al. | 260/944 |
| 4,076,808 | 2/1978 | Lorenz et al. | 260/944 |

Primary Examiner—Anton H. Sutto
Attorney, Agent, or Firm—S. R. LaPaglia; T. G. DeJonghe; S. L. Biggs

[57] ABSTRACT

Compounds of the formula:

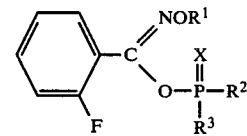

wherein X is sulfur or oxygen; $R^1$ is lower alkyl having from 1 to 3 carbon atoms; $R^2$ is lower alkyl having from 1 to 4 carbon atoms; and $R^3$ is lower alkylthio having from 1 to 4 carbon atoms, are active as insecticides.

21 Claims, No Drawings

PESTICIDAL O-(N-ALKOXY-SUBSTITUTED-ORTHO-FLUORO-BENZIMIDOYL)-THIOPHOSPHONATES

BACKGROUND OF THE INVENTION

This invention relates to certain novel O-(N-alkoxy-substituted-ortho-fluoro-benzimidoyl)-thiophosphonates and their use as insecticides. These compounds are particularly effective in killing a variety of insects.

U.S. Pat. No. 3,760,041 discloses insecticidal and acaricidal compounds of the general formula:

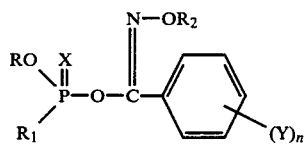

in which
R and $R_2$ each is an alkyl radical of 1 to 6 carbon atoms,
$R_1$ is an alkyl or alkoxy radical of 1 to 6 carbon atoms,
X is an oxygen or sulfur atom,
n is an integer from 0 to 5, and
Y is a halogen atom, an alkyl radical to 1 to 4 carbon atoms or a nitro group.

U.S. Pat. No. 3,872,185 discloses insecticidal and acaricidal compounds of the general formula:

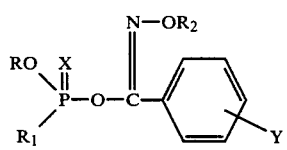

in which
R and $R_2$ each independently is alkyl of 1 to 6 carbon atoms,
$R_1$ is alkyl or alkoxy of 1 to 6 carbon atoms,
X is oxygen or sulfur, and Y is lower alkoxy or alkylmercapto.

U.S. Pat. No. 4,076,808 discloses insecticidal and acaricidal compounds of the general formula:

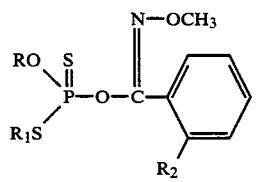

in which
R and $R_1$ each independently is alkyl with 1 to 4 carbon atoms, and
$R_2$ is hydrogen or nitro.

Preferably R is ethyl and $R_1$ is alkyl with 3 or 4 carbon atoms.

U.S. Pat. No. 4,054,650 discloses a compound of the formula:

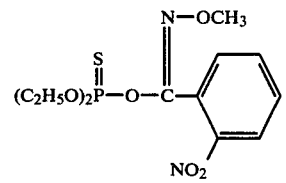

which possesses arthropodicidal properties.

U.S. Pat. No. 4,327,089 discloses a group of insecticidal and acaricidal compounds having the general formula:

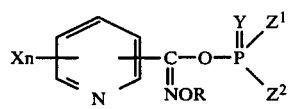

wherein X is halogen, lower alkyl, lower acyloxy, trifluoromethyl or nitro; n is 0, 1, 2 or 3, y is O or S; R is lower alkyl; and $Z^1$ and $Z^2$ each are lower alkoxy, lower alkylthio, phenyl optionally substituted with lower alkyl, phenoxy, haloalkoxy or alkylamino.

My commonly-assigned, copending U.S. patent application Ser. No. 393,216, filed June 28, 1982, now U.S. Pat. No. 4,478,832 discloses O-(N-alkoxy-substituted-benzimidoyl)-phosphorus esters and thioesters and thioesters of the formula:

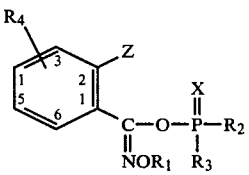

wherein X is sulfur or oxygen; $R_1$ is lower alkyl, lower alkynyl, or benzyl optionally substituted with 1 to 3 halogen atoms; $R_2$ is lower alkyl, lower alkoxy or lower alkylthio; $R_3$ is lower alkoxy, lower alkylthio, lower alkylamino or phenyl; and $R_4$ is hydrogen, cyano, trifluoromethyl, halogen, carboxyalkyl or nitro, and Z is hydrogen, cyano, trifluoromethyl, carboxyalkyl, nitro, $S(O)_nR_5$ or $SO_2NR_6R_7$ where n is 1 or 2, $R_5$ is lower alkyl and $R_6$ and $R_7$ are independently hydrogen or lower alkyl; provided that when $R_1$ is lower alkyl and $R_3$ is alkoxy, then $R_4$ and Z are not both hydrogen or if $R_4$ is hydrogen, Z is not nitro; and provided further that if $R_1$ is lower alkyl, $R_2$ is alkyl or alkoxy and $R_3$ is alkoxy, then if Z is hydrogen or nitro, $R_4$ is not nitro or halogen, as insecticidal.

SUMMARY OF THE INVENTION

The pesticidal O-(N-alkoxy-substituted-orthofluoro-benzimidoyl)-thiophosphonates of this invention are represented by the formula:

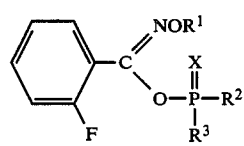

wherein X is sulfur or oxygen; $R^1$ is lower alkyl having from 1 to 3 carbon atoms; $R^2$ is lower alkyl having from 1 to 4 carbon atoms; and $R^3$ is lower alkylthio having from 1 to 4 carbon atoms.

Among other factors, the present invention is based upon my surprising finding that the compounds of the present invention having an ortho-fluoro-substitution on the benzene ring and an alkylthio group bonded to the phosphorus atom are particularly effective as insecticides and acaricides (miticides), particularly as compared with certain other O-(N-alkoxy-substituted-benzimidoyl)-phosphorus esters and thioesters (see compound 11C, Tables I to IV). More particularly, the compounds of my invention are especially effective as miticides and aphidicides.

Preferred $R^1$ groups include methyl and ethyl.

Preferred $R^2$ groups include methyl, ethyl and isopropyl.

Preferred $R^3$ groups include methylthio, ethylthio, isopropylthio and isobutylthio.

Preferred compounds include those where $R^2$ is methyl or ethyl and $R^3$ is isopropylthio or isobutylthio. Also preferred are compounds where $R^2$ is isopropyl and $R^3$ is methylthio or ethylthio.

Preferred are compounds where X is sulfur.

DEFINITIONS

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, and the like.

The term "alkenyl" refers to unsaturated alkyl groups having a double bond [e.g., $CH_3CH=CH-CH_2)_2-$] and includes both straight- and branched-chain alkenyl groups. "Lower alkenyl" refers to groups having a total of from 3 to 5 carbon atoms. Typical lower alkenyl groups include, for example propenyl, but-3-enyl, pent-4-enyl, and the like.

Typical lower alkenyl groups include, for example, propenyl, but-3-enyl, pent-4-enyl, and the like.

The term "alkynyl" refers to unsaturated alkyl groups having a triple bond (e.g., $CH_3C\ CCH_2CH_3$) and includes both straight- and branched-chain alkynyl groups. "Lower alkynyl" refers to groups having a total of from 3 to 5 carbon atoms. Typical lower alkynyl groups include propynyl, butynyl, and the like.

The term "alkoxy" refers to the group R'O- wherein R' is alkyl. The term "lower alkoxy" refers to alkoxy groups having from 1 to 6 carbon atoms; examples include methoxy, ethoxy, isopropoxy, and the like.

The term "alkylthio" refers to the group R'S- wherein R' is alkyl. The term "lower alkylthio" refers to alkylthio groups having 1 to 6 carbon atoms; examples include methylthio, ethylthio, isopropylthio, and the like.

The term "alkylamino" refers to the group R'R''N- wherein R' is alkyl and R'' is hydrogen or alkyl. The term "lower alkylamino" refers to alkylamino groups having 1 to 6 carbon atoms. Typical alkylamino groups include methylamino, ethylamino, diethylamino, dimethylamino, and the like.

The term "alkylene" refers to the group $-(CH_2)_x-$ wherein x is an integer greater than zero, and includes, for example, methylene, ethylene, propylene and the like.

The term "carboxyalkyl" refers to the group $-CO_2R'$ is alkyl, preferably having about 1 to about 6 carbon atoms. Typical carboxyalkyl groups include carboxymethyl, carboxyethyl, carboxypropyl and the like.

The terms "insecticide" and "insect" as used herein refer to their broad and commonly understood usages rather than to those creatures which, in the strict biological sense, are classified as insects. Thus, the term "insect" is used not only to include small invertebrate animals belonging to the class "Insecta", but also to other related classes of arthropods, whose members are segmented invertebrates having more or fewer than six legs such as spiders, mites, ticks, centipedes, worms, and the like.

DETAILED DESCRIPTION OF THE INVENTION

The compounds of this invention may be prepared by subjecting the appropriate N-alkoxy-ortho-fluoro-benzimidoyl compounds II to a phosphorylation reaction.

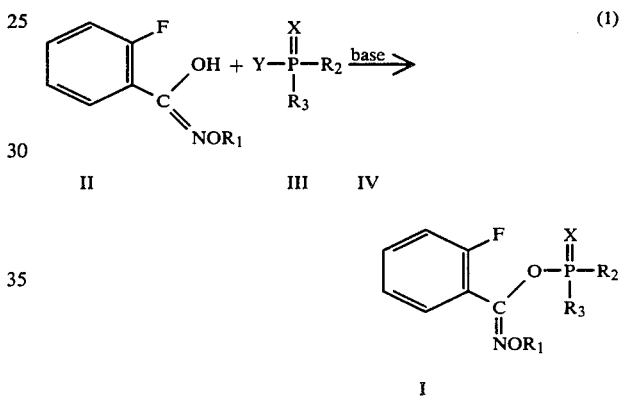

wherein X, $R_1$, $R_2$, and $R_3$, are as defined in conjunction with Formula I and Y is halogen.

The phosphorous reagents have the general formula III wherein X, $R_2$ and $R_3$ are as previously defined and Y is halogen. The phosphorylation reaction is carried out in an inert organic solvent such as methyl ethyl ketone, dimethoxyethane, acetone, acetonitrile, ether, methanol, benzene or toluene. Suitable bases IV used in the phosphorylation reaction include potassium carbonate, sodium hydride, sodium metal and the like. Although equimolar amounts of II, III and IV may be used, it is preferred to have a slight excess of III and IV which results in a better yield and easier workups of the products. Either II or III may be added to the other in the solvent; however, it is preferred to add the phosphorous reagent dissolved in a small amount of solvent to a solution of II and IV. The addition is carried out at temperatures in the range of about 0° to about 40° C. Upon completion of the addition of III, the temperature of the reaction mixture is raised, preferably to reflux (about 80° C.) and the mixture stirred (at reflux) until the reaction is complete, about 4 to about 36 hours.

At completion of the reaction, the solvent is stripped under reduced pressure and heat. The product, a liquid, is then isolated by conventional procedures such as extraction, chromatography and filtration.

The reagents, II, used in the phosphorylation reaction may be prepared according to the following reaction scheme:

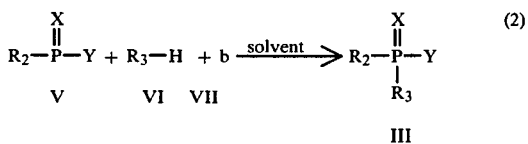

where $R_2$, $R_3$, X and Y are as defined in conjunction with reaction (1) and formula I and b is a base.

Reaction (2) is carried out by combining approximately equimolar amounts of V, VI and VII in solvent. It may be preferred to add a mixture of VI and VII or VII alone slowly in a dropwise manner to a mixture of V or V and VI in solvent. After the addition is complete, the reaction mixture is stirred for an extended period of time, on the order about 16 hours, filtered and the solvent stripped. Suitable solvents include inert organic solvents such as benzene, toluene, and acetonitrile.

The N-alkoxy-ortho-fluoro-benzimidoyl compound II used in the preparation of the compounds of this invention may be prepared according to the following reaction scheme:

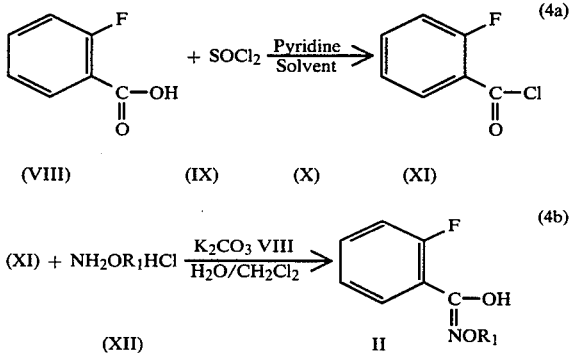

wherein $R_1$ is as defined in conjunction with Formula I.

Reaction (4a) is carried out by warming a stirred mixture of VIII in solvent to about 20° to about 35° C. with a catalytic amount of pyridine X (about 1 ml pyridine per 0.5 mole VIII). To that mixture, a solution of IX in a small amount (about 10 mls) solvent is added dropwise; the resulting mixture is then refluxed for about 6 to about 36 hours. The solvent is stripped and the product XI is obtained free from IX by chasing with toluene. Product XI is immediately dissolved in solvent and used in the second step, reaction (4b) without further isolation. Although roughly equimolar amounts of VIII and IX may be used, it is preferable to use a slight excess of IX.

In reaction (4b), to a mixture of XII and XIII in methylene chloride/water, prepared at low temperature (less than −5° C.), the mixture of XI in solvent is added and the resulting mixture stirred for about 6 to about 36 hours. Although roughly equimolar amounts of XI and XII may be used, it is preferable to use a slight excess of XII.

Reactions (4a) and (4b) are carried out in an inert organic solvent; suitable solvents include, methylene chloride, ether and toluene.

The product II, a solid, may be isolated by conventional procedures such as stripping, extraction, chromatography, filtration and crystallization.

Alternatively, if the acid chloride is commercially available, intermediate II may be prepared using the acid chloride of XI according to reaction 4(b).

UTILITY

The compounds of this invention are surprisingly effective in killing a variety of insects.

The present compounds can be stored and applied as formulations incorporated with compatible biologically inert extenders or carriers such as are typically employed for facilitating dispersion of active ingredients for agricultural chemical applications. These formulations typically contain about from 0.5 to 95 weight % of the present compound, and optionally can contain compatible insecticides, fungicides, etc., and the remainder biologically inert material including dispersing agents, emulsifying agents, wetting agents and carriers.

Such formulations can be formulated as sprays, dusts, or granules and applied to the insects and/or their environment or hosts susceptible to insect attack. They can be formulated as granules of large particle size, as powdery dusts, as wettable powders, as emulsifiable concentrates, as solutions, or as any of several other known types of formulations, depending on the desired mode of application. (Wettable powders generally refer to a form of finely divided particles which disperse readily in water or other dispersant.) Typical carriers include fuller's earth, kaolin clays, silicas, and other highly absorbent, readily wet, inorganic diluents. Typical wetting, dispersing, or emulsifying agents used in agricultural formulations include, for example, the alkyl and alkylaryl sulfonates and sulfonates and their sodium salts; alkylamide sulfonates, including fatty methane taurides, alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface active agents are available in commerce. The surface active agent, when used, normally comprises from one percent to fifteen percent by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains about 65–80 weight % silica and 35–20 weight % of the compound(s) of the invention.

Useful liquid concentrates include the emulsifiable concentrates, which are homogeneous liquid or paste compositions which are readily dispersed in water to other dispersant, and can consist entirely of the compound(s) of the invention with a liquid or solid emulsifying agent, or can also contain a liquid carrier, such as xylene, heavy aromatic naphthas, isophorone, and other non-volatile organic solvents. These concentrates are usually dispersed in water, or their liquid carrier, and then applied as a spray or paint to the area to be treated.

Other useful formulations include simple solutions of the active compound in a dispersant in which it is completely soluble at the desired concentration, such as acetone, alkylated naphthalenes, xylenes, or other organic solvents.

Optimum formulation concentrations and the manner and frequency of application may vary somewhat with the particular species of insect, the degree of infestation, the environment, including type of soil, soil conditions and weather conditions (e.g., rain fall), and can be obtained by routine experimentation.

A further understanding of my invention can be had from the following non-limiting examples.

EXAMPLE 1

Preparation of

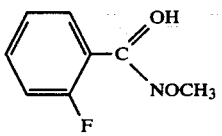

N-methoxy-2-trifluorobenzhydroxamic Acid

To a stirred mixture of 30.3 g (0.363 moles) methoxyamine hydrochloride and 51 g (0.37 moles) potassium carbonate in about 300 ml water/methylene chloride maintained at a temperature below $-5°$ C., 50 g (0.32 moles) 2-fluoro-benzoylchloride were dropped in. The reaction mixture was then allowed to stir at room temperature overnight. The aqueous and methylene chloride layers were separated. The methylene chloride layer was dried over magnesium sulfate, filtered and stripped to give about 45 g of the above-identified product, as a clear amber liquid.

Elemental analysis for $C_8H_8FNO_2$ showed: calculated %C 56.8, %H 4.77, and %N 8.28; found %C 57.54, %H 5.37, and %N 8.69.

EXAMPLE 2

Preparation of

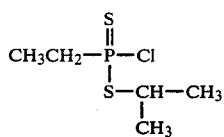

Ethyl-S-isopropylphosphonothioic Chloride

To a mixture of 326 g (2.0 moles) ethylphosphonothioic dichloride in 500 ml acetonitrile, a mixture of 152.3 g (2.0 moles) 2-propanethiol and 158.2 g (2.0 moles) pyridine were added over a period of 20 minutes. The reaction mixture was stirred overnight at room temperature and then heated at reflux for four hours, resulting in the formation of solids. The reaction mixture was cooled to room temperature and then filtered. The filtrate was combined with 500 ml hexane, washed twice with 75 ml water and then stripped to give 373 g of the aboveidentified product as a yellow oil.

EXAMPLE 3

Preparation of

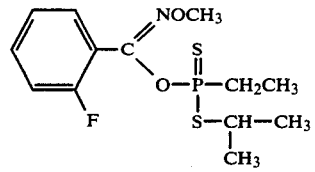

S-Isopropyl-O-(N-methoxy-2-fluorobenzimidoyl)-ethanethionophosphonate

A mixture of 4.2 g (0.025 moles) N-methoxy-2-fluorobenzyhydroxamic acid and 4.2 g (0.03 moles) potassium carbonate in about 100 ml methyl ethyl ketone were stirred together and heated (to about reflux) for about one hour. Into the resulting mixture, 5.3 g (0.026 moles) ethyl-S-isopropylphosphonothiotic chloride were dropped; the reaction mixture was the refluxed about 8 hours. The methyl ethyl ketone was stripped off under reduced pressure and heat. Water (about 50 ml) and methylene chloride (about 100 ml) were added to the residue and the resulting mixture was stirred. The layers were separated. The methylene chloride layer was dried with magnesium sulfate, filtered and stripped to give the crude product. Chromatography on a silica gel column gave the above-identified product as a clear, colorless liquid.

Elemental analysis for $C_{13}H_{19}FNO_2PS_2$ showed: calculated %C 46.6, %H 5.71, and %N 4.17; found %C 47.05, %H 6.55, and %N 3.8.

EXAMPLE 4

Preparation of

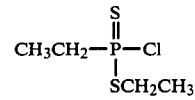

Ethyl-S-ethylphosphonothioic chloride

To a stirred mixture of 81.5 g (0.5 moles)

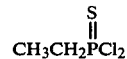

(ethylphosphonothioic dichloride), and 74 ml ethanethiol in about 400 ml benzene in a round bottom flask in an ice bath, 71 ml triethylamine was slowly added dropwise. The reaction mixture was allowed to stir at room temperature for about 24 hours. The reaction mixture was filtered and the solvent was stripped under reduced pressure and heat. Acetone (about 50 to 60 ml) was added to the residue, and the resulting mixture was stirred. The mixture was filtered to remove salts and the acetone was stripped to the crude product. Chromatography on a silica gel column eluting with hexane with 5% methylene chloride gave the product a clear light liquid.

Elemental analysis for $C_4H_{10}ClPS_2$ showed: calculated %C 25.5, %H 5.34, and %N 0; found %C 20.41, %H 5.42 and %N 0.03.

EXAMPLE 5

Preparation of

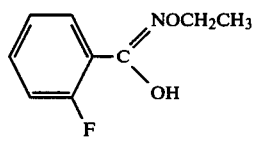

N-Ethoxy-2-fluorobenzhydroxamic Acid

To a mixture of 35 g (0.36 moles) ethoxyamine hydrochloride, 51 g (0.37 moles) potassium carbonate and ice chips (about 100 g) which had been stirred for several minutes, 50 g (0.32 moles) 2-fluoro-benzoylchloride in methylene chloride (about 50 ml) were added dropwise. The reaction mixture was allowed to come to room temperature and then was stirred at room temperature for about three to four hours. The aqueous and methylene chloride layers were separated. The methylene chloride layer was dried with magnesium sulfate, filtered and stripped under reduced pressure to give about 82 g of the above-identified product as a clear light yellow liquid.

Elemental analysis for $C_9H_{10}FNO_2$ showed: calculated %C 59.0; %H 55, and %N 7.65; found %C 59.1; %H 5.67, and %N 7.84.

By following the procedures described in the Detailed Description of the invention and in Examples 1 to 5, the following compounds are made:

S-isopropyl-O-(N-methoxy-2-fluorobenzimidoyl)-methanethionophosphonate;
S-isobutyl-O-(N-methoxy-2-fluorobenzimidoyl)-ethanethionophosphonate;
S-isobutyl-O-(N-methoxy-2-fluorobenzimidoyl)-methanethionophosphonate;
S-methyl-O-(N-methoxy-2-fluorobenzimidoyl)-isopropanethionophosphonate;
S-ethyl-O-(N-methoxy-2-fluorobenzimidoyl)-isopropanethionophosphonate;
S-isopropyl-O-(N-ethoxy-2-fluorobenzimidoyl)-ethanethionophosphonate
S-isopropyl-O-(N-ethoxy-2-fluorobenzimidoyl)-methanethionophosphonate;
S-isobutyl-O-(N-ethoxy-2-fluorobenzimidoyl)-ethanethionophosphonate;
S-isobutyl-O-(N-ethoxy-2-fluorobenzimidoyl)-methanethionophosphonate;
S-methyl-O-(N-ethoxy-2-fluorobenzimidoyl)-isopropanethionophosphonate;
S-ethyl-O-(N-ethoxy-2-fluorobenzimidoyl)-isopropanethionophosphonate;
S-isopropyl-O-(N-methoxy-2-fluorobenzimidoyl)-ethanephosphonate;
S-isopropyl-O-(N-methoxy-2-fluorobenzimidoyl)methanephosphonate;
S-isobutyl-O-(N-methoxy-2-fluorobenzimidoyl)-ethanephosphate;
S-isobutyl-O-(N-methoxy-2-fluorobenzimidoyl)-methanephosphonate;
S-methyl-O-(N-methoxy-2-fluorobenzimidoyl)-isopropanephosphonate;
S-ethyl-O-(N-methoxy-2-fluorobenzimidoyl)-isopropanephosphonate;
S-isopropyl-O-(N-ethoxy-2-fluorobenzimidoyl)-ethanephosphonate
S-isopropyl-O-(N-ethoxy-2-fluorobenzimidoyl)-methanephosphonate;
S-isobutyl-O-(N-ethoxy-2-fluorobenzimidoyl)-ethanephosphonate;
S-isobutyl-O-(N-ethoxy-2-fluorobenzimidoyl)-methanephosphonate;
S-methyl-O-(N-ethoxy-2-fluorobenzimidoyl)-isopropanephosphonate; and
S-ethyl-O-(N-ethoxy-2-fluorobenzimidoyl)-isopropanephosphonate.

EXAMPLE A

Aphid Control

Compounds of this invention were tested for their insecticidal activity against cottom aphids (*Aphis gossypii* Glover). An acetone solution of the test compound containing a small amount of non-ionic emulsifier was diluted with water to give a concentration of 40 ppm. Cucumber leaves infested with cotton aphids were dipped in the test compound solution. Mortality readings were taken after 24 hours. The results expressed as % control, are tabulated in Table I.

EXAMPLE B

Mite Control

Compounds of this invention were tested for their insecticidal ability against two-spotted mites (*Tetranychus urticae*). An acetone solution of the test compound containing a small amount of non-ionic emulsifier was diluted with water to give a concentration of 40 ppm. Lima bean leaves which were infested with mites were dipped in the test compound solution. Mortality readings were taken after 24 hours. The results, expressed as % control, are tabulated in Table I.

EXAMPLE C

Mite Egg Control

Compounds of this invention were tested for their ovicidal activity against eggs of the two-spotted spider mite (*Tetranychus urticae*. An acetone solution of the test toxicant containing a small amount of non-ionic emulsifier was diluted with water to give a concentration of 40 ppm. Two days before testing, 2-week old lima bean plants were infested with spider mites. Two days after infestation, leaves from the infested plants are dipped in the toxicant solution, placed in a petridish with filter paper and allowed to dry in the open dish at room temperature. The treated leaves were then held in covered dishes at about 31° to 33° C. for seven days. On the eighth day egg mortality readings are taken. The results, expressed as % control, are tabulated in Table I.

EXAMPLE D

Housefly

Compounds of this invention were tested for their insecticidal activity against the housefly (*Musca domestica* L.). A 500 ppm acetone solution of the test compound was placed in a microsprayer (atomizer). A random mixture of anesthetized male and female flies was placed in a container and 55 mg of the above-described acetone solution was sprayed on them. A lid was placed on the container. A mortality reading was then taken after 24 hours. The results are expressed as % control and are reported in Table I.

EXAMPLE E

American Cockroach

Compounds of this invention were tested for their insecticidal activity against the American cockroach (*Periplaneta americana L.*). A 500 ppm acetone solution of the test compound was placed in a microsprayer (atomizer). A random mixture of anesthetized male and female roaches was placed in a container and 55 mg of the above-described solution was sprayed on them. A lid was placed on the container. A mortality reading was made after 24 hours. The results, expressed as % control, are reported in Table I.

EXAMPLE F

Alfalfa Weevil

Compounds of this invention were tested for their insecticidal activity against the alfalfa weevil (*H. Brunneipennis Boheman*). A 500 ppm acetone solution of the test compound was placed in a microsprayer (atomizer). A random mixture of male and female weevils was placed in a container and 55 mg of the above-described acetone solution was sprayed on them. A lid was placed on the container. A mortality reading was made after 24 hours. The results are expressed as % control and are tabulated in Table I.

EXAMPLE G

Cabbage Looper

Compounds of this invention were tested for their insecticidal activity against cabbage looper (*Trichoplusia ni*). An acetone solution of the test compound containing a small amount of non-ionic emulsifier was diluted with water to give a concentration of 500 ppm. Excised cucumber leaves were dipped in the test compound solution and allowed to dry. The leaves were then infested with cabbage looper larvae. Mortality readings were taken after 24 hours. The results are expressed as % control and are reported in Table I.

EXAMPLE H

Control of Mosquito Larvae

The compounds of this invention were tested for control of mosquito larvae (*Aedes aegypti*). A plastic cup was filled with 90 ml deionized water and then infested with early 4th-stage mosquito larvae contained in 10 ml water. One rabbit food pellet was added to the cup to provide food for the larvae. A 200 microliter aliquot of a 500 ppm solution of the test compound was added to the cup. The water was then thoroughly mixed to give a final concentration of test compound of 0.1 ppm. The cup was covered with a plastic lid in order to prevent evaporation and to confine any subsequently emerging adult mosquitos. The cup was kept at 27° C. for 6 days at which time mortality readings were taken. The results, expressed as % control, are reported in Table I.

EXAMPLE I

Leaf Dip - Cotton Aphid

Compounds were tested for their insecticidal activity against the cotton aphid [*Aphis gossypii (Glover)*] on excised cucumber leaves. An acetone solution of the test compound containing a small amount of nonionic emulsifier was diluted with water to give a starting concentration of 100 ppm. The 100 ppm was further diluted with water to give a dilution series of 10 ppm, 4 ppm, 1.6 ppm and 0.64 ppm.

Well-infested, but vigorous cucumber leaves were selected from the stock-colony rearing room and were cut into pieces large enough so that two such pieces just about cover the base of each petri dish unit. Each piece was immersed in a toxicant solution of known concentration, 4 pieces (replicates) per toxicant concentration. The pieces were dried (but not dessicated) by placement under a hood. Then, each leaf piece was moistened lightly and placed in an incubator at 75° F. for 24 hours. Infested leaf pieces which had been dipped in a mixture of acetone, non-ionic emulsifier but no test compound served as check treatments.

After incubation, a field of 20 aphids was located on each treated leaf piece and the number of dead in the field counted. From the numbers killed, the average kill and % control per treatment were calculated which were then used to calculate the LD 50 and LD 90 for the test compound.

Results are tabulated in Table II.

EXAMPLE J

Foliar Residue Weathering - Cotton Aphid

Compounds were tested to determine the effective residual insecticidal activity against Cotton Aphids [*Aphis gossypii (Glover)*] on cucumbers.

An acetone solution of test compound was diluted with water (which contained a small amount of non-ionic emulsifier) to give solutions containing 2000 ppm and 1000 ppm test compound. Pots, each containing 3 cucumber plants (having first trifoliater or second growth about 1 inch long) were sprayed with a test compound solution, 4 pots (replicates) for each concentration of each test compound. After spraying, the plant foliage was allowed to dry; then the plants were placed in a greenhouse maintained at 75°–80° C. Treated plants were challenged by taping an aphid-infested leaf (from a stock colony) onto a primary leaf of one plant per pot, 24 hours after treatment and at weathering intervals of 3 and 7 days after treatment for an exposure period of 24 hours.

Mortality counts were made 24 hours after exposure to treated plants. Percent control was calculated as the average percent mortality based on a random mortality count of 20 insects per replicate. After evaluation after 24 hours exposure, the infested leaves were removed and discarded. The results are tabulated in Table III.

EXAMPLE K

Leaf Dip - Mites

Compounds were tested for their acaricidal activity against parathion-resistant two-spotted spider mites [*Tetranychus urticae (Koch)*] on excised lima bean leaves. An acetone solution of the test compound containing a small amount of non-ionic emulsifier was diluted with water to give a starting concentration of 100 ppm. The 100 ppm was further diluted with water to give a dilution series of 40 ppm, 16 ppm, 6.4 ppm and 2.5 ppm.

Well-infested, but vigorous, small lima bean leaves were selected from the stock-colony rearing room and were cut into pieces large enough so that two such pieces just about cover the base of each petri dish unit. Each piece was immersed in a toxicant solution of known concentration, 4 pieces (replicates) per toxicant concentration. The pieces were dried (but not dessicated) by placement under a hood. Then, each leaf piece was moistened lightly and placed in an incubator at 75° F. for 24 hours. Infested leaf pieces which had been dipped in a mixture of acetone, non-ionic emulsifier but no test compound served as check treatments.

After incubation, a field of 20 aphids was located on each treated leaf piece and the number of dead in the field counted. From the numbers killed, the average kill and % control per treatment were calculated which were then used to calculate the LD 50 and LD 90 for the test compound.

Results are tabulated in Table IV.

EXAMPLE L

Foliar Residue Weathering - Mites

Compounds were tested to determine the effective residual acaricidal activity against parathion-resistant two-spotted spider mites [*Tetranychus urticae* (Koch)] on pinto beans.

An acetone solution of test compound was diluted with water (which contained a small amount of non-ionic emulsifier) to give solutions containing 2000 ppm and 1000 ppm test compound. Pots, each containing 3 bean plants (having first trifoliater or second growth about 1 inch long) were sprayed with a test compound solution, 4 pots (replicates) for each concentration of each test compound. After spraying, the plant foliage was allowed to dry; then the plants were place din a greenhouse maintained at 75°-80° C. Treated plants were challenged by taping a miteinfested leaf (from a stock colony) onto a primary leaf of one plant per pot, 24 hours after treatment and at weathering intervals of 3 and 7 days after treatment for an exposure period of 24 hours.

Mortality counts were made 24 hours after exposure to treated plants. Percent control was calculated as the average percent mortality based on a random mortality count of 20 mites per replicate. After evaluation after 24 hours exposure, the infested leaves were removed and discarded. The results are tabulated in Table V.

EXAMPLE M

Contact Foliar Spray - Mite

Compounds were tested to determine acaricidal activity when applied as a single foliar spray on pinto bean plants infested by parathion-resistant two-spotted spider mites [*Tetranychus urticae* (Koch)].

An acetone solution of test compound was diluted with water containing a small amount of non-ionic emulsifier to give solutions containing 2000 ppm and 1000 ppm test compound.

Three days before treatment, 2-week old bean plants were infested with mites by taping an infested leaf from a stock colony onto a primary leaf of one bean plant in a pot (3 plants per pot).

Three days after infestation, the plants (4 pots or replicates per concentration per compound) were treated by spraying with a test compound solution using a linear spray chamber. After spraying, the plant foliage was allowed to dry; the plants were then placed in a greenhouse maintained at 75°-85° F.

Population control measurements were made using a 0-10 rating system by comparing adult mite populations existing on the treated plants with the adult mite populations present on the untreated check plants at 24 hours after treatment and then at 7-day intervals.

The results, expressed as percent control are given in Table VI.

TABLE I

| | Insecticidal Activity | | | | | | | | |
|---|---|---|---|---|---|---|---|---|---|
| | A | AS | MA | ME | HF | AR | AW | CL | ML |
| 1  39885 | 100 | 0 | 80 | 45 | 100 | 0 | 20 | 80 | 70 |
| 11C 36648 | 85 | 0 | 85 | 55 | 0 | 0 | 0 | 0 | 0 |

A = Aphid
AS = Aphid Systemic
MA = Mite Adult
ME = Mite Egg
HF = Housefly
AR = American Cockroach
AW = Alfalfa Weevil
CL = Cabbage Looper
ML = Mosquito Larvae

TABLE II

| | Cotton Aphid Leaf Dip | | |
|---|---|---|---|
| | | Standards LD/50/80 | |
| Compound | LD50/90 | Orthene | Dibron |
| 1  39855 | 0.25/1.7 | 0.5/3.5 | 0.26/1.2 |
| 11C 36648 | 0.8/16 | 0.7/3.5 | 1.1/3.2 |

TABLE III

Cotton Aphid Foliar Residue Weathering

| Compound | Dose (ppm) | Days | | |
|---|---|---|---|---|
| | | 1 | 3 | 7 |
| 1  39855 | 2000 | 100 | 86 | 51 |
| | 1000 | 100 | 58 | — |
| 11C  36648 | 2000 | — | — | — |
| | 1000 | — | — | — |

TABLE IV

Mite Adult Leaf Dip

| Compound | LD50/90 | Standards LD/50/90 | |
|---|---|---|---|
| | | Plictran | Parathion |
| 1  39855 | 6/40 | 4.0/13 | 22% @ 100 |
| 11C  36648 | 24/372 | 4.7/12 | 23% @ 100 |

TABLE V

Foliar Residue - Mite

| Compound | Dose (ppm) | Days | | | |
|---|---|---|---|---|---|
| | | 1 | 3 | 7 | 10 |
| 1  39855 | 2000 | 98 | 88 | — | 46 |
| | 1000 | 74 | 76 | — | 9 |

TABLE VI

Mite Adult Foliar Spray

| Compound | Dose (ppm) | Days | | |
|---|---|---|---|---|
| | | 1 | 3 | 14 |
| 1  39855 | 2000 | 100 | 100 | 100 |
| | 1000 | 100 | 100 | 98 |
| Plictran | 2000 | 100 | 100 | 100 |
| | 1000 | 100 | 100 | 100 |

What is claimed is:

1. A compound of the formula $$\underset{F}{\underset{|}{\text{C}_6\text{H}_4}}-\underset{O-P(=X)(R^2)(R^3)}{\text{C}(=NOR^1)}$$

wherein X is sulfur or oxygen/ $R^1$ is lower alkyl having from 1 to 3 carbon atoms; $R^2$ is lower alkyl having from 1 to 4 carbon atoms; and $R^3$ is lower alkylthio having from 1 to 4 carbon atoms.

2. A compound according to claim 1 wherein $R^2$ is methyl or ethyl and $R^3$ is isopropylthio or isobutylthio.

3. A compound according to claim 2 wherein X is sulfur.

4. A compound according to claim 3 wherein $R^1$ is methyl or ethyl.

5. A compound according to claim 4 wherein $R^1$ is methyl.

6. A compound according to claim 5 wherein $R^3$ is isopropylthio.

7. A compound according to claim 6 wherein $R^2$ is ethyl.

8. A compound according to claim 6 wherein $R^2$ is methyl.

9. A compound according to claim 1 wherein $R^2$ is isopropyl and $R^3$ is methylthio or ethylthio.

10. A compound according to claim 9 wherein X is sulfur.

11. A compound according to claim 10 wherein $R^1$ is methyl or ethyl.

12. A method of killing insects which comprises contacting said insect or its environment with an insecticidally effective amount of a compound of claim 1.

13. A method of killing insects which comprises contacting said insect or its environment with an insecticidally effective amount of a compound of claim 2.

14. A method of killing insects which comprises contacting said insect or its environment with an insecticidally effective amount of a compound of claim 7.

15. A method of killing insects which comprises contacting said insect or its environment with an insecticidally effective amount of a compound of claim 8.

16. A method of killing insects which comprises contacting said insect or its environment with an insecticidally effective amount of a compound of claim 9.

17. A composition for killing insects comprising a biologically inert carrier and an insecticidally effective amount of a compound of claim 1.

18. A composition for killing insects comprising a biologically inert carrier and an insecticidally effective amount of a compound of claim 2.

19. A composition for killing insects comprising a biologically inert carrier and an insecticidally effective amount of a compound of claim 7.

20. A composition for killing insects comprising a biologically inert carrier and an insecticidally effective amount of a compound of claim 8.

21. A composition for killing insects comprising a biologically inert carrier and an insecticidally effective amount of a compound of claim 9.

* * * * *